United States Patent [19]

McClane

[11] Patent Number: 5,442,967
[45] Date of Patent: Aug. 22, 1995

[54] SIDE-STREAM SAMPLING DEVICE

[76] Inventor: M. Brent McClane, 3504 W. Main St., Belleville, Ill. 62223

[21] Appl. No.: 200,194

[22] Filed: Feb. 22, 1994

[51] Int. Cl.⁶ .......................... G01N 1/20; G01N 1/18
[52] U.S. Cl. .................................. 73/863.22; 73/864; 435/292
[58] Field of Search ............... 73/863.21, 863.22, 864, 73/863.31, 863.41, 863.71, 863.43, 863.51, 863.52, 863.53, 864.51, 864.91; 435/30, 292, 293, 294

[56] References Cited

U.S. PATENT DOCUMENTS

| | | | |
|---|---|---|---|
| 2,294,655 | 9/1942 | Einstein | 73/864.63 |
| 2,660,063 | 11/1953 | Sawers | 73/864.51 |
| 2,959,523 | 11/1960 | Decker et al. | 435/292 |
| 4,762,009 | 8/1988 | Scrndto | 73/864.51 X |
| 4,864,877 | 4/1989 | Ortiz et al. | 73/863.52 |
| 5,219,390 | 6/1993 | McClane | 73/864 |
| 5,343,768 | 9/1994 | McClane | 73/864 |
| 5,347,877 | 9/1994 | Gadbois | 73/863.52 |

FOREIGN PATENT DOCUMENTS

| | | | |
|---|---|---|---|
| 117429 | 6/1986 | Japan | 73/864.63 |
| 140959 | 6/1988 | Japan | 73/863.21 |
| 1484074 | 8/1977 | United Kingdom | 73/864.51 |
| 1154210 | 5/1985 | U.S.S.R. | 73/864 |
| 1180736 | 9/1985 | U.S.S.R. | 73/864.63 |

OTHER PUBLICATIONS

Robar Machine, Inc. advertising flyer showing in FIG. 5 a side stream sampling device. 1 page, published by May 1994.
AquaTech Environmental advertising flyer listing a side stream bio-box. 2 pages, published by May 1994.

Primary Examiner—Thomas P. Noland
Attorney, Agent, or Firm—Armstrong, Teasdale, Schlafly & Davis

[57] ABSTRACT

A side-stream sampling device for taking biologic samples from a stream of water, the sampling device comprising an elongate box, having first and second ends, and an open top. A lid sealingly closes the open top of the box. There is an inlet at the first end of the box and an outlet at the second end of the box, the outlet extending upwardly to a point vertically above the top of the box to create a backpressure to keep the box full. A plurality of sampling surfaces are removably mounted inside the box for accumulating plant and/or animal specimens from the water flowing through the box.

5 Claims, 7 Drawing Sheets

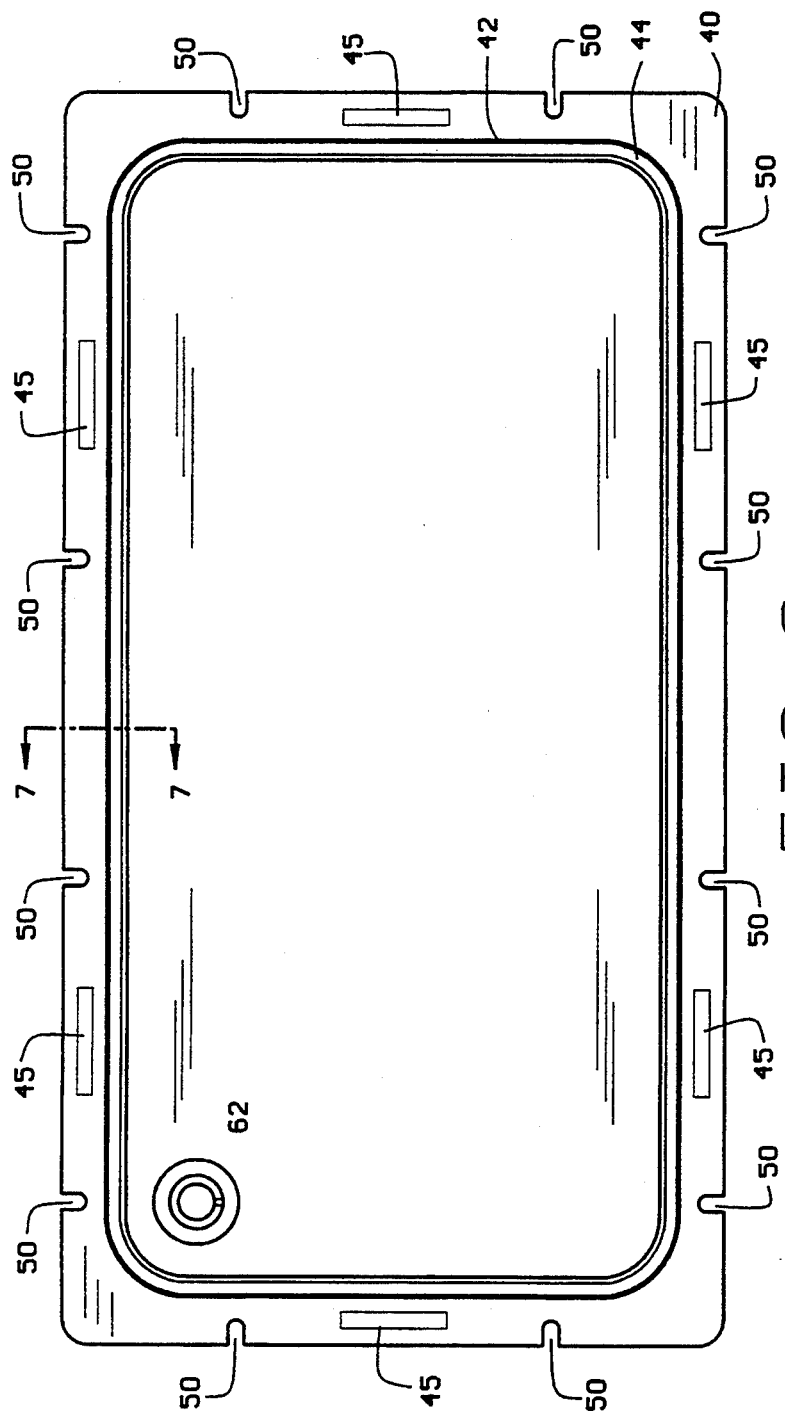
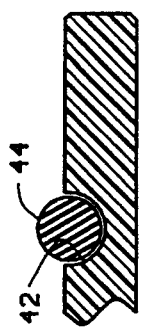
FIG. 6
FIG. 7

SIDE-STREAM SAMPLING DEVICE

BACKGROUND OF THE INVENTION

This invention relates to a sampler device and method for monitoring a stream of water representative of a larger flow, for the presence of plant and/or animal life.

It is sometimes desirable to sample water, for example the water flowing into the intake of a water treatment facility, a power facility, or other industrial facility, for the presence or absence of plant and/or animal life. Of particular recent concern is monitoring water delivery systems for the presence of zebra mussels, *Dreissena polymorpha*. Veligers and post-veligers, the immature stages of the zebra mussel, are only approximately 60 to 200 microns, and thus difficult to detect in water. However, zebra mussels are very fast growing, with few natural enemies. If zebra mussels are not detected early so that countermeasures can be taken, it is entirely possible for the zebra mussels to completely block a water delivery system, and otherwise interfere with the operation of a facility dependent on water. Thus it is important to monitor water entering an intake for the presence of zebra mussels so that countermeasures can be taken, or where countermeasures (such as the introduction of chlorine) have been taken, to monitor the effectiveness of those countermeasures.

Some attempts have been made to provide side-stream sampling devices, but these devices have usually been crude. For example existing side-stream sampling devices have been open, and thus were noisy and leaky. Moreover, they would not accurately emulate conditions in a closed water system. Furthermore, the water level was at the level of the water outlet, giving rise to distracting noise.

SUMMARY OF THE INVENTION

Generally, the sampler device of the present invention comprises an elongate box, having first and second ends, and an open top. The device further includes a lid that sealingly closes the open top of the box. There is an inlet at the first end of the box, and an outlet at the second end of the box. The outlet extends above the top of the box to create a backpressure to keep the box full of water. A plurality of sampling surfaces are removably mounted inside the box for accumulating plant and/or animal specimens from the water flowing through the box.

These sampling devices are preferably positioned at various locations inside the box which experience different flow conditions, for example in relatively stagnant areas and in relatively high flow areas. To this end, one or more baffles can be provided in the box to direct the flow of water through the box. Preferably there is at least one baffle extending transversely across the box, intermediate the inlet and the outlet to direct water flowing through the box across at least one sampling surface.

The box is preferably operated while sealed and substantially completely filled with water. The device has a recloseable valve in the upper portion of the box or in the lid, to allow air in the box to be bled out to facilitate substantially completely filling the box with water. The lid has a sealing gasket adapted to surround the opening in the top of the box forming a water-tight seal. A plurality of over-center latches are provided around the perimeter of the device. The latches are adapted to hold the lid against the top of the box, compressing the gasket to form a seal between the lid and the box.

According to the method of monitoring water passing through a system for plant and/or animal life of this invention, a portion of the water is diverted through the sampler device comprising an elongate box, having first and second ends, and an open top; a lid that sealingly closes the open top of the box; a water inlet at the first end of the box for delivering water to the box; and a water outlet at the second end of the box for removing water from the box, the outlet extending upwardly to a point vertically above the top of the box to create a backpressure to keep the box full of water; and a plurality of sampling surfaces removably mounted inside the box for accumulating plant and/or animal specimens from the water flowing through the box. The sampling surfaces are periodically removed from the box and examined for evidence of plant or animal life.

The sampler device according to this invention provides a closed sampling environment closely emulating the water system from which the sample is taken. The closed box operates more quietly and is less prone to leaks than prior sampling devices. The sampler can include baffles, so that sampling surfaces are present in a variety of flow conditions. These and other features and advantages will be in part apparent, and in part pointed out hereinafter.

BRIEF DESCRIPTION OF THE DRAWINGS

FIG. 6 is a bottom plan view of the lid;

FIG. 7 is a partial cross-sectional view of the lid taken along the plane of line 7—7 in FIG. 6;

Corresponding reference numerals indicate corresponding parts throughout the several views of the drawings.

DETAILED DESCRIPTION OF THE PREFERRED EMBODIMENT

Figure 1:
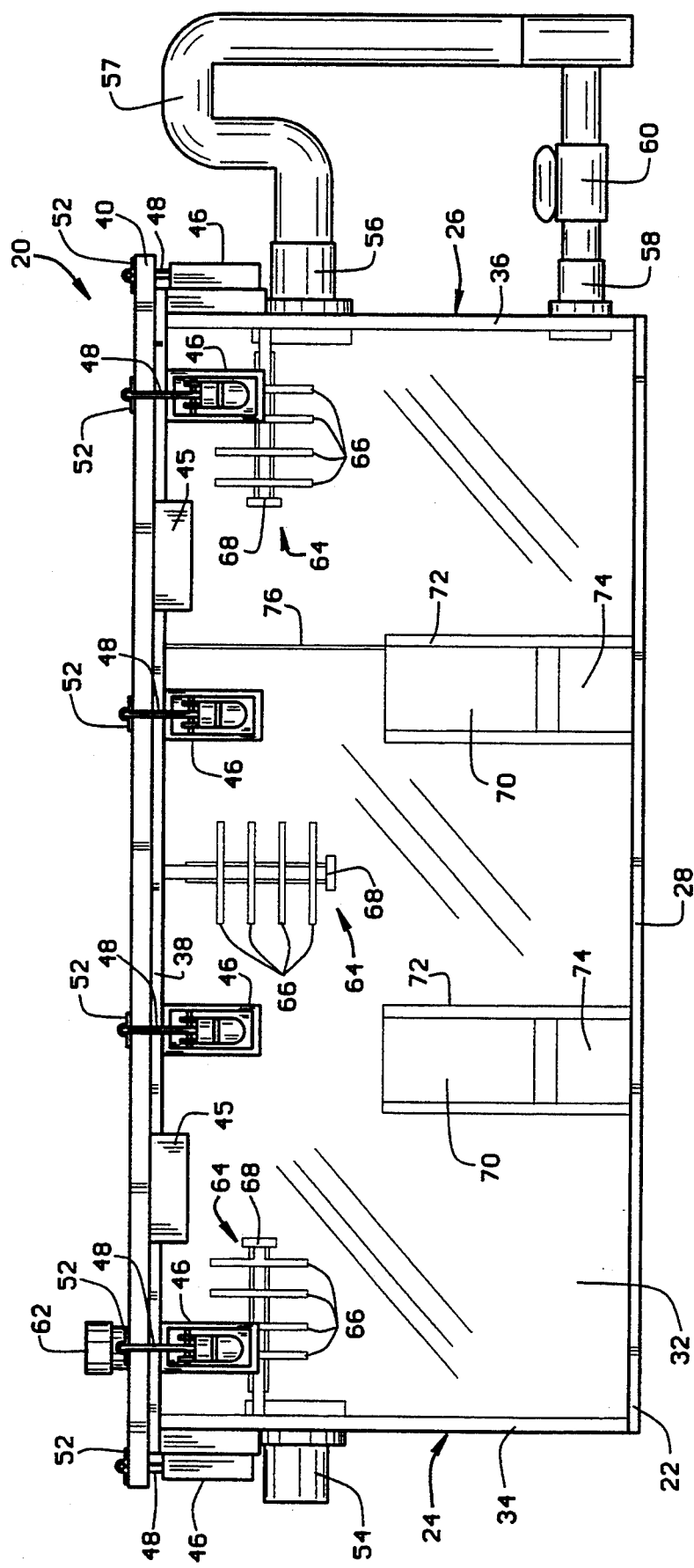
FIG. 1 is a side elevation of a side-stream sampler device constructed according to the principles of this invention.
Figure 2:
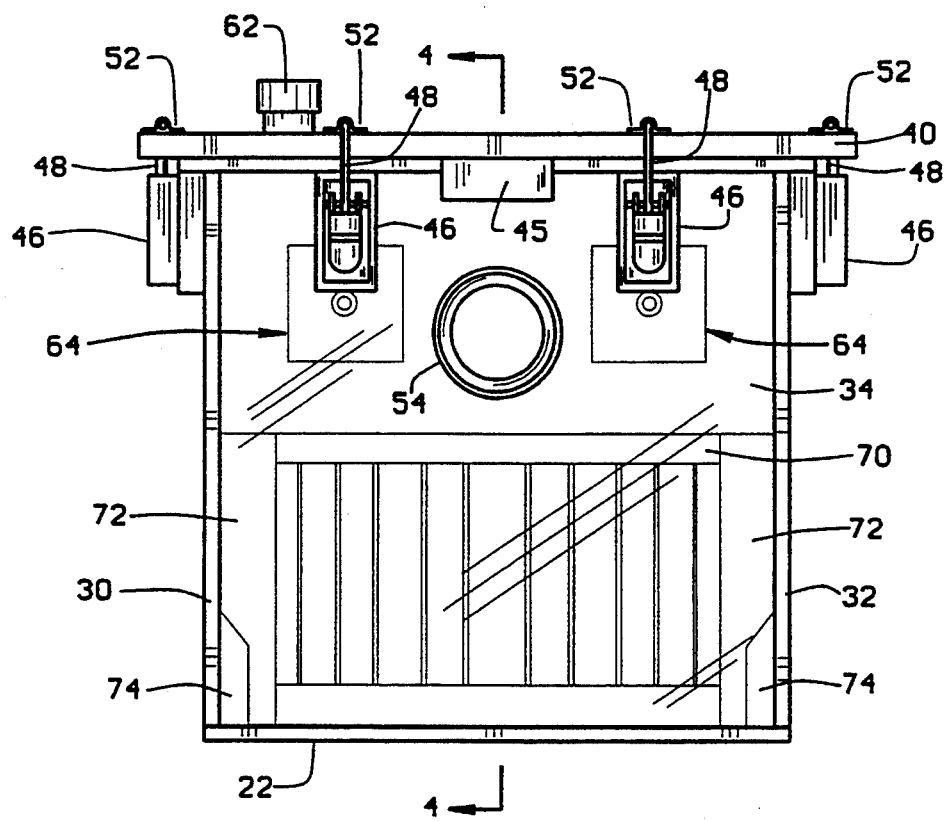
FIG. 2 is a first end elevation view of the sampler device.

A side-stream sampler device constructed according to the principles of this invention is indicated generally as 20 in FIG. 1. The side-stream sampler device 20 is adapted to receive a stream of water diverted from the water delivery system of, for example, a water purification facility, an electrical power facility, or other industrial facility. The sampler device provides a way of monitoring the water entering the facility for plant and/or animal life.

Figure 5:
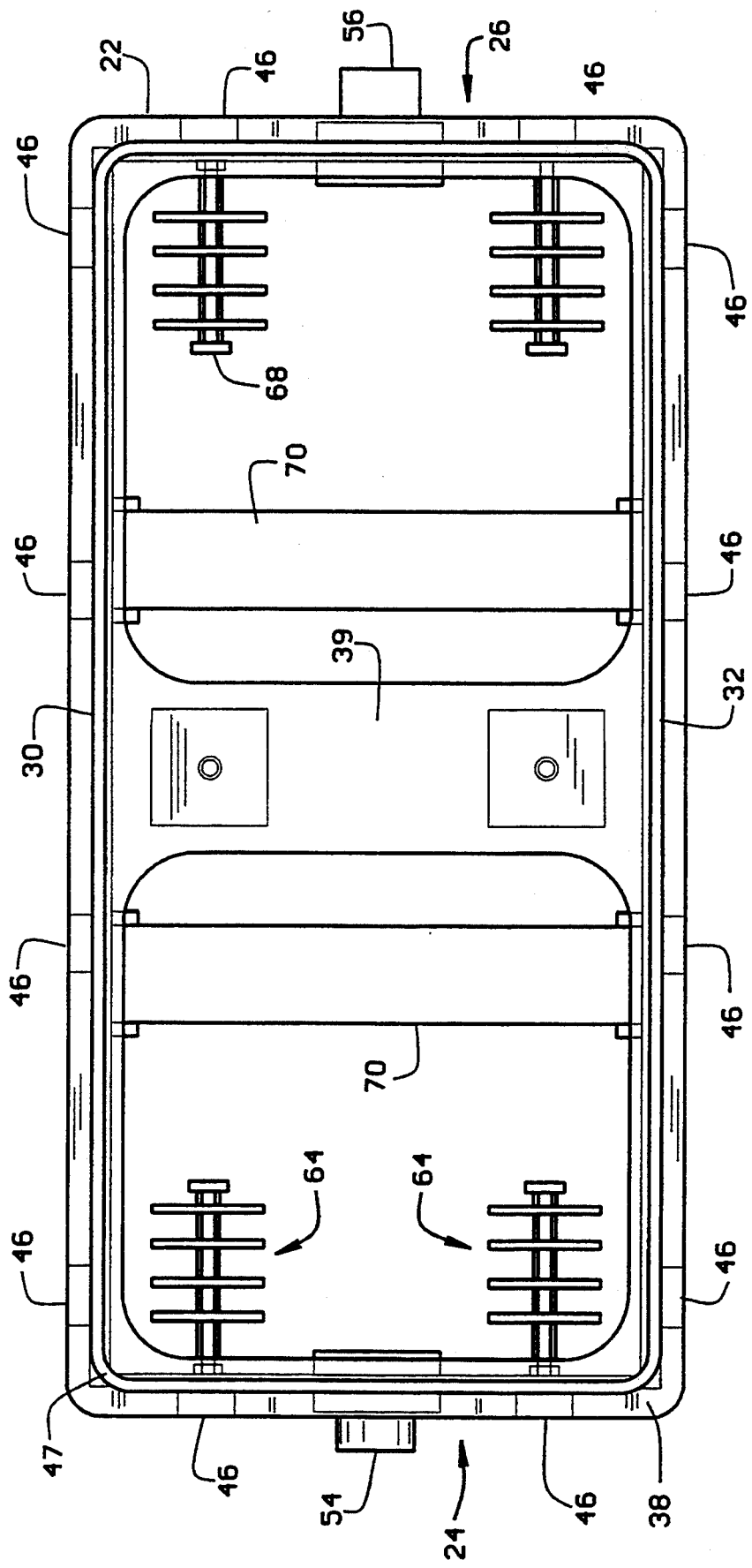
FIG. 5 is a top plan view of the sampler device without the lid.
Figure 8:
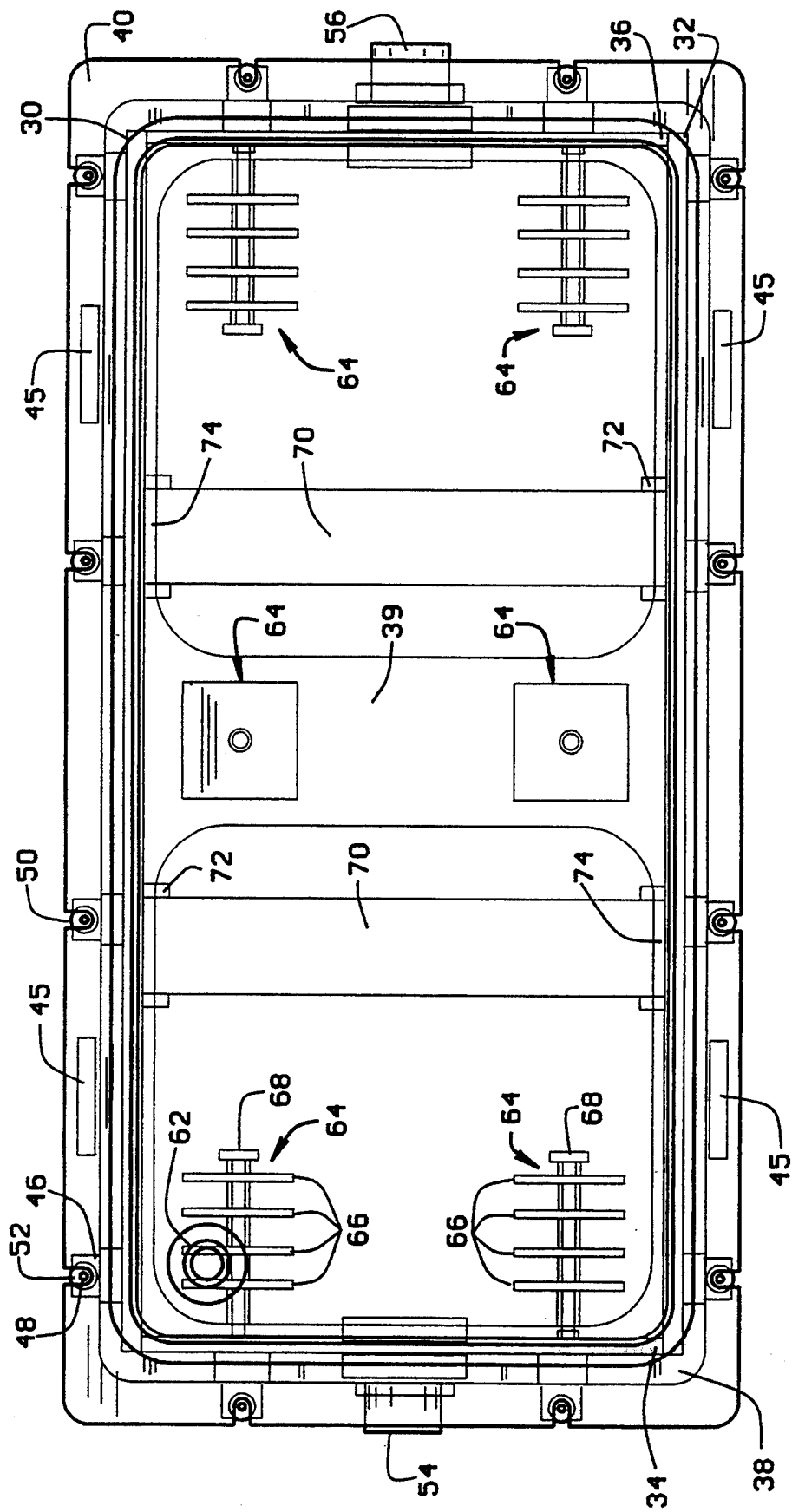
FIG. 8 is a top plan view of the sampler device.
Figure 9:
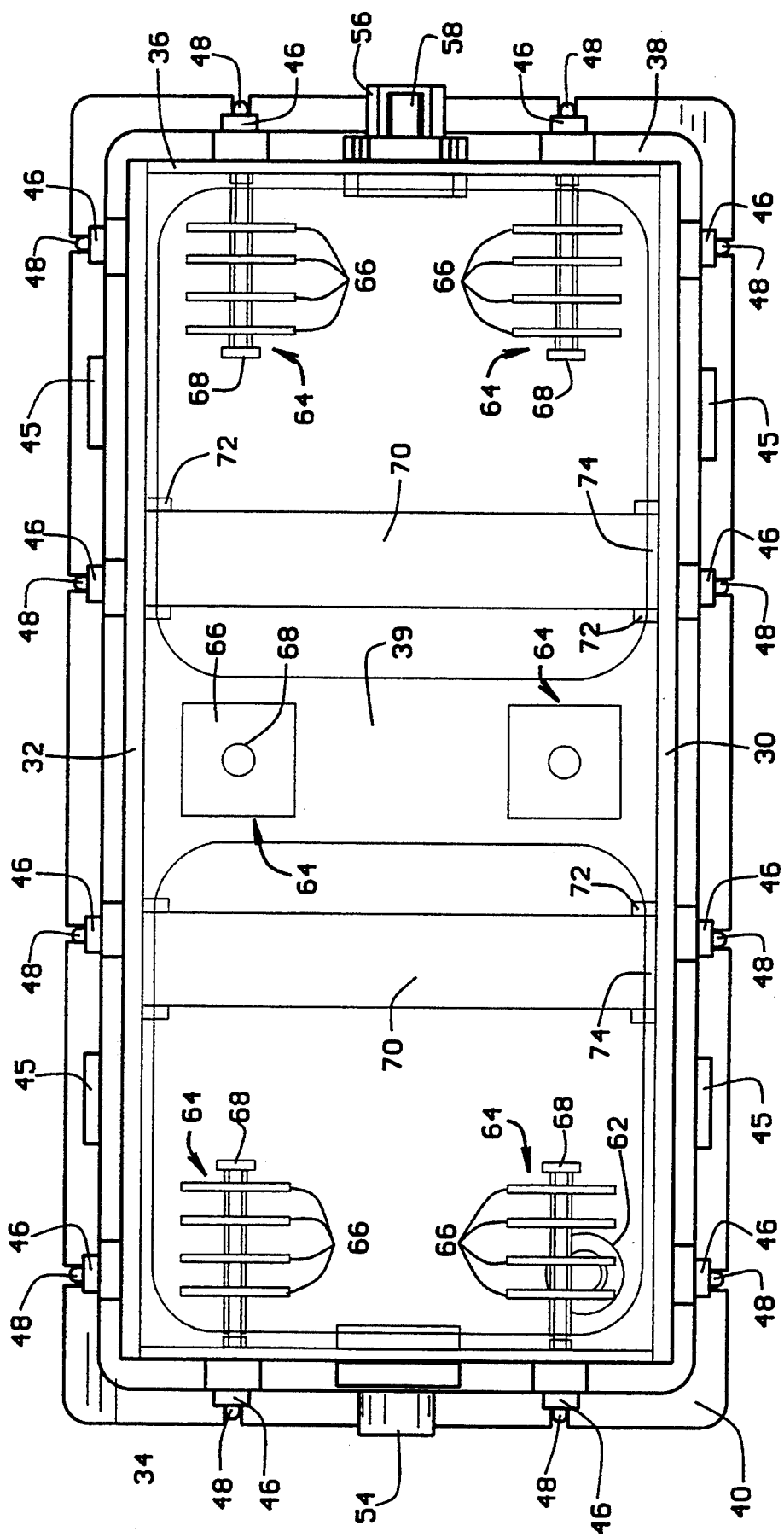
FIG. 9 is a bottom plan view of the sampler device.

As shown in FIG. 1, the sampler device 20 comprises an elongate box 22, having first and second ends 24 and 26, respectively. In this preferred embodiment the box 22 is in the shape of a rectangular prism, with a bottom panel 28, left and right side panels 30 and 32, and first and second end panels 34 and 36. These panels may be made of a polymer material such as polymethyl methacrylate, adhesively joined together. The panels can be transparent to facilitate visual inspection of the interior or the panels can be translucent or opaque. The top of the box 22 is open, but as shown in FIG. 5, a top plate 38 is mounted in the upper edges of the plates. The top plate 38 has a cross member 39 extending between the left and right side panels 30 and 32, to add rigidity to the box 22, and preventing the left and right side panels from bowing outwardly when the box is filled with water.

A lid 40 is adapted to be mounted over the top of the box. The lid may be made from the same material as the box. As best shown in FIG. 6, the underside of the lid has a groove 42 in which a sealing gasket 44 is mounted. The sealing gasket can be made from an elastomeric material and can be an o-ring. The sealing gasket surrounds the opening in the top of the box 22, to seal the opening and close the box. There are a plurality of over-center clamps 46 on the side panels and end panels. The clamps 46 have stems 48 that extend through notches 50 in the periphery of the lid 40, and grippers 52 on the ends of the stems that grip the surface of the lid around the notches to hold the lid tightly against the top of the box, compressing the gasket 44 to form a water-resistant seal between the box and the lid. A plurality of tabs 45 depend downwardly from the underside of the lid 40, for centering the lid over the box 22. The tabs help ensure that the gasket 44 aligns with a grove 47 in the top plate 38.

There is an inlet 54 at the first end 24, extending through the first end panel 34, generally adjacent the top of the panel. The inlet 54 has a generally T-shaped cross-section secured in the end panel 34 with a nut. There is an outlet 56 at the second end 26, extending through the second end panel 36, generally adjacent the top of the panel. The outlet 56 has a generally T-shaped cross-section, secured in the end panel 36 with a nut. The outlet includes a tube 57 extending to a vertical height equal to, or preferably slightly above the top of the box 22 to provide a backpressure to maintain the box full of water. The tube 57 can be made of a flexible material to facilitate assembly. A drain 58 is also provided in the second end 26, extending through the second panel 36, generally adjacent the bottom of the panel. The drain 58 has a generally T-shaped cross-section secured with a nut. The drain 58 connects with the tube 57 of outlet 56, and has a valve 60 therein for opening and closing the drain.

There is a recloseable valve 62 at the top of the box which can be opened to bleed out air from the sealed box to allow the box to substantially completely fill with water. Once the box 22 is filled, the valve 62 can be closed to prevent water from leaking from the box.

Figure 3:
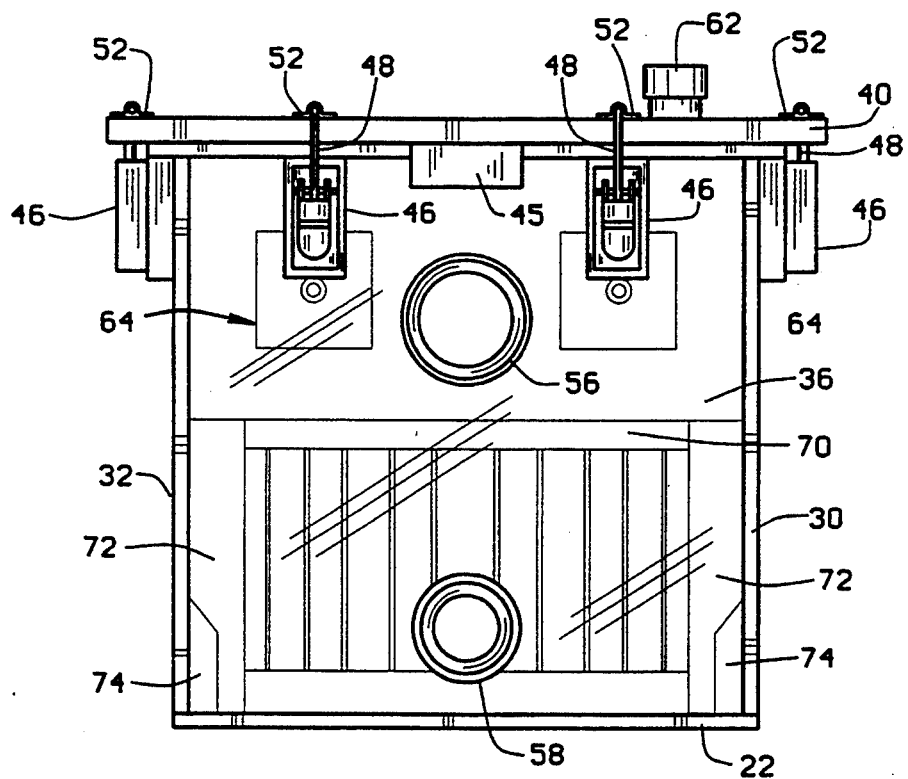
FIG. 3 is a second end elevation view of the sampler device.
Figure 4:
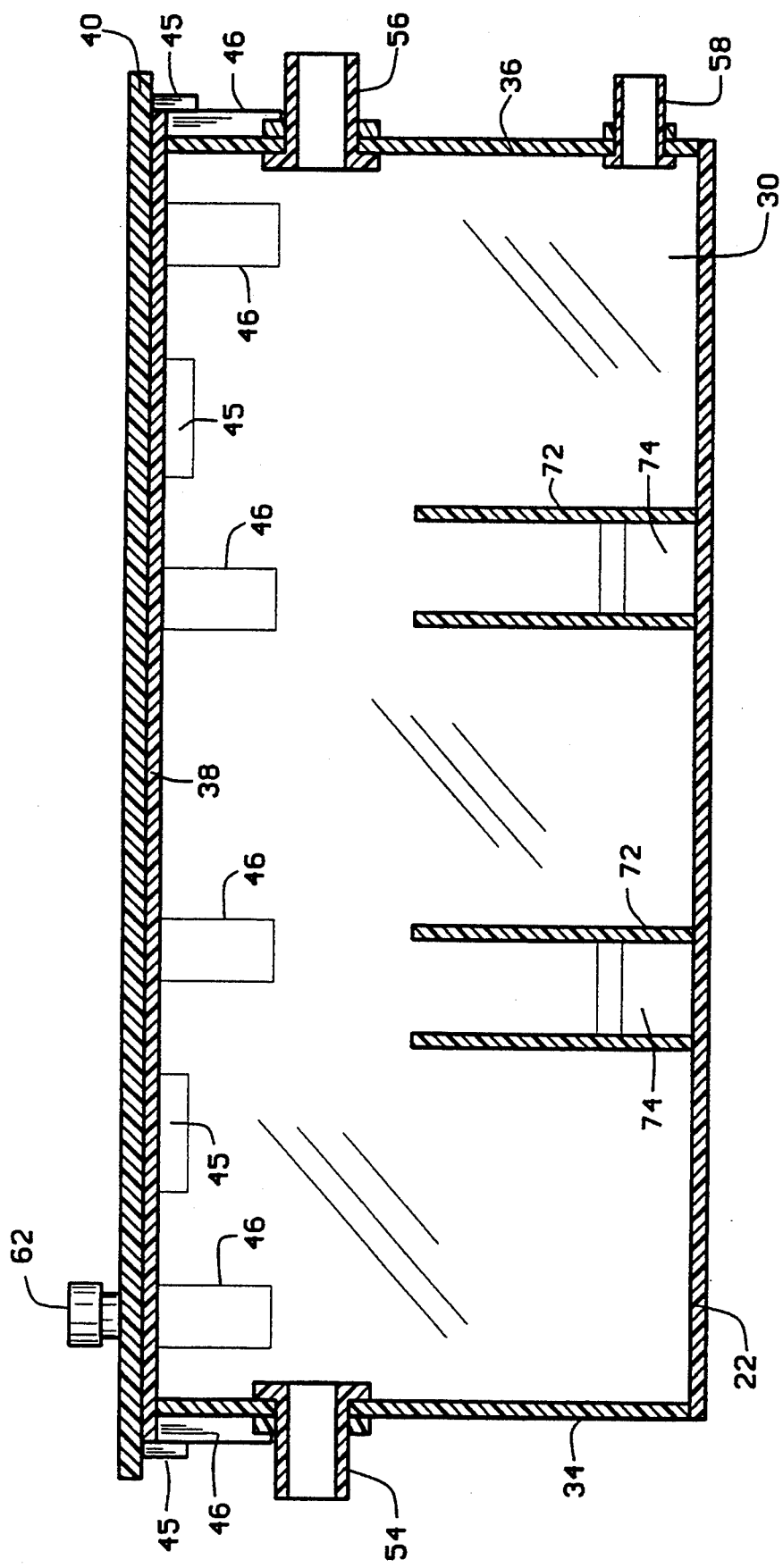
FIG. 4 is a longitudinal cross-sectional view of the sampler device taken along the plane of line 4—4 in FIG. 2.

There are a plurality of sampling surfaces disposed inside the box. Plant and animal life, for example veligers, can settle on these surfaces. The area of the sampling surfaces is preferably standardized, so that comparisons can be made about plant and/or animal population densities. One such sampling surface can be a stack 64 of plates 66 that are 5.08 cm by 5.08 cm, stacked on a rod 68 with 0.7126 $cm^2$ spacers. Mounting fixtures can be provided on the side walls and end walls of the box, and even on the underside of the top plate 38 to mount these stacks 64. These mounting fixtures may be threaded nuts into which the rods can be threaded. Additional sampling surface can be provided by using a sampling device 70, like those described in U.S. Pat. No. 5,219,390, or like that described in application Ser. No. 07/922,026, filed Jul. 27, 1992, now U.S. Pat. No. 5,343,768, the disclosures of which are incorporated herein by reference. Brackets 72 can be provided on the side panels 30 and 32, to mount the sampler devices 70 so that they extend across the box, transverse to the flow from the inlet 54 to the outlet 56. Spacers 74 (see FIG. 3) can be mounted in the brackets 72, to center samplers 70 in the brackets 72. The sampler devices 70 are simply slid into and out of the brackets.

A baffle 76 can be mounted transversely across the box 22, between the side panels 30 and 32, intermediate the inlet 54 and the outlet 56 to divert the water flowing through though the box. The baffle 76 diverts water flow though one of the sampler devices 70 held in the brackets 72, and creates areas of protected or stagnant flow for other samplers. This allows population samples to be taken in various flow conditions, as various plants and animals have preferences for different flow conditions.

The lid 40 of the box 22 is easily removed by releasing the clamps 46 and lifting the lid from the box. The open top provides easy access to remove the sampling surfaces for study and replacing the sampling surfaces with new ones. The lid is easily replaced, and the box refilled for further operation.

OPERATION

The sampler device 20 of this invention is easily set up by connecting the device 20 to a by-pass from the flow through a water system, such as the water delivery system to a power generation facility. The desired sampling surfaces are installed inside the box 22, the lid 40 is placed on the box, and the clamps 46 are operated to seal the lid on the box. The recloseable valve 62 is opened to allow air inside the box to escape so that the box can be substantially completely filled with water. The configuration of the outlet provides backpressure so that water level can rise above the level of the opening of the outlet. When the box is substantially completely full, the recloseable valve can be closed to prevent leaks.

The closed environment inside the box is essentially the same as the closed water system from which the water is diverted. Thus the deposition of plants and animals on the sampling surfaces in the box are representative of what is taking place in the water system. From time to time the lid 40 can be quickly and easily removed to remove one or more of the sampling surfaces, and perhaps replace the surfaces removed with new sampling surfaces. The device can be used to simply monitor the water quality, for example for the presence of zebra mussels, or to monitor the effectiveness of countermeasures.

I claim:

1. A side-stream sampling device for taking biological samples from a stream of water, the sampling device comprising:
    an elongate box, having first and second ends, and an open top;
    a lid that sealingly closes the open top of the box;
    an inlet at the first end of the box;
    an outlet at the second end of the box, the outlet extending upwardly to a point vertically above the top of the box to create a backpressure to keep the box full;
    a plurality of sampling surfaces removably mounted inside the box for accumulating plant and/or animal specimens from the water flowing through the box.

2. The side-stream sampling device according to claim 1 further comprising a recloseable valve in an upper portion of the box or the lid, to allow air in the box to be bled out to facilitate filling the box with water.

3. The side-stream sampling device according to claim 1 further comprising a baffle extending transversely across the box, intermediate the inlet and the outlet to direct water flowing through the box across at least one of said sampling surfaces.

4. The side-stream sampling device according to claim 1 wherein the lid comprises a sealing gasket adapted to surround the opening in the top of the box forming a water-tight seal.

5. The side-stream sampling device according to claim 1 further comprising a plurality of over-center latches adapted to hold the lid against the top of the box, compressing the gasket to form a seal between the lid and the box.

* * * * *